United States Patent [19]

Bridges et al.

[11] 4,105,919
[45] Aug. 8, 1978

[54] SPECTROPHONE WITH FIELD TUNING OF ABSORPTION CELL

[75] Inventors: Thomas James Bridges, Holmdel; Ernest Gardner Burkhardt, Wall, both of N.J.

[73] Assignee: Bell Telephone Laboratories, Incorporated, Murray Hill, N.J.

[21] Appl. No.: 790,460

[22] Filed: Apr. 25, 1977

[51] Int. Cl.$^2$ .............................. G01J 1/00; G01J 3/42
[52] U.S. Cl. .................................... 250/341; 250/343; 356/96
[58] Field of Search ............... 250/343, 344, 345, 346; 356/96, 97

[56] References Cited
U.S. PATENT DOCUMENTS 3,700,890  10/1972  Kruezer .............................. 250/341
3,937,577  2/1976  Dorsch .............................. 356/96

Primary Examiner—Alfred E. Smith
Assistant Examiner—Janice A. Howell
Attorney, Agent, or Firm—David I. Caplan

[57] ABSTRACT

The spectrophone, in which a gas containing an impurity in an absorption cell is illuminated by an optical beam that is modulated at an acoustic frequency, has an output pressure response at the acoustic frequency in accordance with the concentration of the impurity in the gas. This output is tuned by a magnetic (or electric) field applied to the absorption cell, while the optical wavelength is kept constant. The Zeeman (or Stark) effect of the impurity can thus be used to tune the absorption process of the impurity to a maximum response.

11 Claims, 2 Drawing Figures

SPECTROPHONE WITH FIELD TUNING OF ABSORPTION CELL

FIELD OF INVENTION

This invention relates to the field of optical absorption spectroscopy, and more particularly to optical infrared absorption systems for detecting impurities in a gaseous medium such as air pollution detection apparatus.

BACKGROUND OF INVENTION

The "spectrophone" is useful as apparatus for detecting traces of an impurity in a gas medium, such as nitric oxide (NO) pollutant in air. The spectrophone includes an absorption cell containing the gas medium, upon which is incident optical radiation, typically infrared, which is modulated at an acoustic frequency. For example, laser radiation from a carbon monoxide laser is modulated in intensity at 150 Hz by a mechanical chopper. The useful output of the absorption cell is in the form of pressure variations at the acoustic frequency, generated in the gas by the absorption of the modulated light by the impurity. These pressure variations are detected with a microphone. In such a system, however, it is very unlikely that the laser wavelength will ordinarily coincide with the optimum absorption wavelength ("absorption line") of the impurity; therefore, ordinarily a continuously tunable laser, such as a spin flap Raman laser, must be used as the optical radiation source, in order to enable an exact coincidence to be obtained. The use of such tunable lasers as optical sources in general is commercially undesirable from the standpoints of apparatus complexity and expense. Accordingly, it would be desirable to have spectrophone apparatus for air pollution detection without the need for tuning of the laser source.

SUMMARY OF INVENTION

Tuning of the laser source in a spectrophone for detecting an impurity in a gas is avoided by tuning the absorption process of the impurity molecule, as by applying a static magnetic (or electric) field in the gas, thereby relying on the Zeeman (or Stark) effect to tune the absorption process itself. By "static" field is meant a field which, although adjustable in field strength, contains appreciable Fourier components only at frequencies below the response of the microphone. In this way, a suitable field applied to the gas medium changes the resonant absorption wavelength and thereby brings the optimum absorption wavelength into at least near coincidence with a fixed wavelength laser source whose output is modulated at an acoustic frequency.

The optical modulation in this invention can be optical polarization modulation at the acoustic frequency, instead of optical intensity modulation, since the Zeeman (or Stark) effect is dependent upon optical polarization. The use of polarization modulation has the advantage that it tends to suppress spurious signals produced by the optical absorption in the windows of the absorption cell of the spectrophone, because the absorption of the Zeeman (or Stark) components by the impurities in the gas is anisotropic (polarization dependent) and thus discriminates against the isotropic (polarization independent) absorption in the spectrophone windows. Thus, the use of optical polarization modulation has the advantage of better signal-to-noise ratio in the response. Moreover, when using either optical intensity or optical polarization modulation in the practice of this invention, the signal-to-noise ratio is improved by reason of the fact that the responses of the pollutant impurities to be detected are highly sensitive to the static magnetic (or electric) field, whereas the background response due to water vapor or other gases present in relatively high concentration is not thus sensitive to the static magnetic (or electric) field. Accordingly, the background noise is reduced in the usual case of air pollution detection.

In a specific embodiment of the invention, a carbon monoxide (CO) laser provides an infrared beam of substantially monochromatic linear polarized radiation at a wavelength approximately corresponding to an optical absorption transition of nitric oxide. The plane of optical polarization of this beam is modulated, for example, by means of passage through a half-wave plate rotating at a first acoustic frequency $f$ and hence modulating the polarization at a second acoustic frequency $2f$. The resulting polarization modulated beam is incident upon a transparent window of an absorption cell full of gas, typically air or nitrogen, which contains nitric oxide (NO) as a trace impurity. A static magnetic field is applied to the cell of field strength sufficient to produce, through the Zeeman effect, at least near resonance absorption of the radiation by the molecules of nitric oxide. By "at least near resonance" is meant that, whereas in the absence of the applied magnetic field virtually no detectable optical absorption occurs, in the presence of a suitable value of this magnetic field significant absorption occurs sufficient to produce detectable pressure variations in the gas. These pressure waves have an acoustic frequency $4f$ and are detected by a microphone coupled to the gas in the absorption cell.

BRIEF DESCRIPTION OF THE DRAWING

This invention, together with its features, advantages, and objects, can be better understood from the following detailed description when read in conjunction with the drawing in which.

Figure 1:
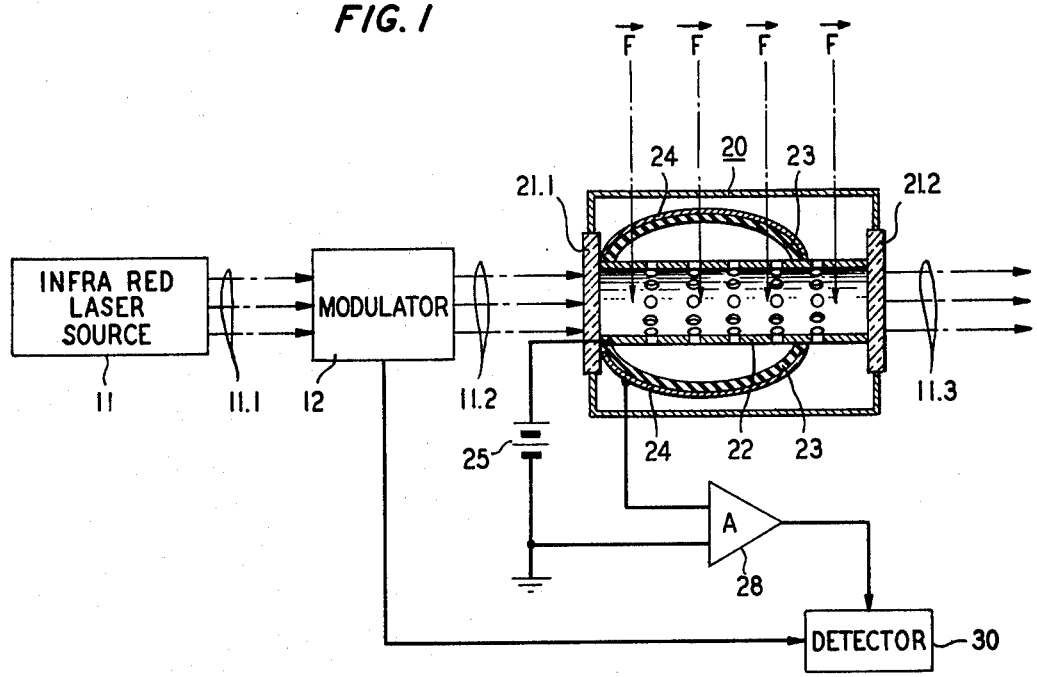
FIG. 1 shows, partly in cross section, a system for detecting impurities in a gas, in accordance with a specific embodiment of the invention.

For the sake of clarity only, the drawing of FIG. 1 is not to scale.

DETAILED DESCRIPTION

As shown in FIG. 1, an optical absorption cell 20 is filled with air or other gas, typically at a pressure of about 20 mm Hg or more, containing nitric oxide (NO) to the extent of about 20 ppm or less as the impurity to be detected. An infrared carbon monoxide laser source 11 provides a linearly polarized optical beam 11.1 of about 400 milliwatts continuous wave having an optical frequency that corresponds to about 1884.35 cm$^{-1}$ reciprocal wavelength. This optical frequency is fairly close to the transition $v = 1\leftarrow0$, $J = 5/2\leftarrow3/2$ of the vibrational rotational state of $^2\pi_{3/2}$ of the NO molecule. A modulator 12 modulates the optical beam at an acoustic frequency preferably in the range of about 20 Hz to 500 Hz. For example, the modulator 12 is a half-wave plate rotating at a frequency of 15 revolutions per second to provide a modulated optical beam 11.2 whose plane of polarization is rotating at a frequency of $2 \times 15 = 30$ Hz. The modulated optical beam 11.2 is focused, typically by a lens (not shown), upon an optical entrance window 21.1 at the optical entrance end of the absorption cell 20. The modulated optical beam traverses the gas in the cell 20 and exits as beam 11.3 through the optical exit window 21.2 at the optical exit end of the absorption cell 20. These windows 21.1 and 21.2 are typically composed of essentially barium fluoride, $BaF_2$.

The absorption cell 20 is advantageously vacuum tight and includes a circularly cylindrically shaped metal tube 22 containing the gas under test. The cell also has inlet and outlet means (not shown) for introducing and exhausting gas into and out of the cell, as known in the art. A static (but adjustable) magnetic field $\vec{F}$ is applied to the gas in the tube by means of an iron cored magnet (not shown) capable of applying fields of up to 2 kilogauss. For example, this static field can be a linear ramp having a ramp time of the order of about 10 minutes or more, and a field direction perpendicular to the optical propagation direction. The tube 22 is provided with a plurality of apertures to enable coupling of the gas pressure variations with a coaxial cylindrical microphone in the form of metallized dielectric, such as aluminized mylar. Specifically, this microphone comprises a dielectric insulating mylar layer 23 surrounded by a metal aluminum layer 24. The microscopic distance between the dielectric layer 23 and the wall of the tube 22 is exaggerated in FIG. 1, in order to show that some of the gas in the tube can leak out into the microscopically small space therebetween, thereby forming a variable capacitance microphone. For example, the metal tube 22 is 1 cm in diameter and is 15 cm long, wrapped with aluminized mylar 0.001 inches thick. A battery 25 supplies a voltage bias of about 180 volts to the capacitor formed by the dielectric mylar layer 23 together with the metal layer 24 and the metal tube 22.

During operation, electrical signals are produced by the varying capacitance in the microphone, in response to the pressure variations in the gas caused by optical absorption from the modulated beam by the impurity in the gas. These pressure variations are at the acoustic modulation frequency $4 \times 15 = 60$ Hz determined by the modulator 12. Thus, the useful signals of the microphone are likewise at this acoustic frequency and are fed to an amplifier 28. After amplification, the amplified signals are fed to an A.C. detector 30 sensitive to both amplitude and phase of the electrical output signals of the amplifier 28 at the acoustic frequency. The detector 30 is advantageously synchronized with the modulation frequency or a multiple thereof obtained from the modulator 12, in order to synchronize the phase of the modulator with the phase of the detector.

Figure 2:
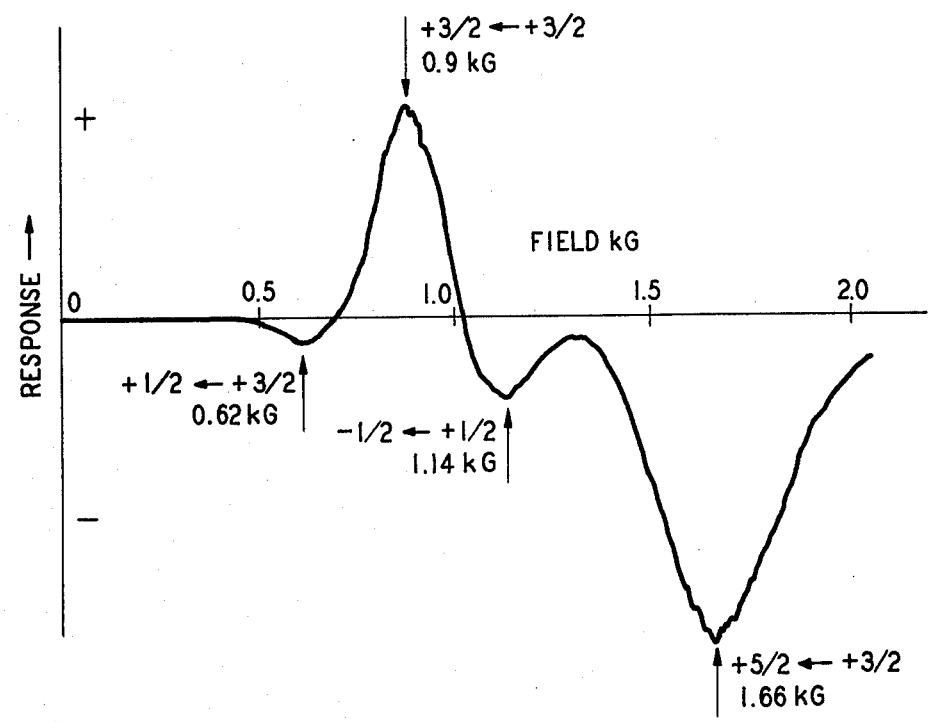
FIG. 2 shows a plot of output response versus magnetic field obtained in a practice of the system illustrated in FIG. 1.

As shown in FIG. 2 for the case of nitric oxide impurity, the response of the detector (in arbitrary units) is strongly dependent upon the static magnetic field $\vec{F}$. The maxima of the magnitude of the response are of opposite phase (opposite algebraic sign) for the $\Delta M = 0$ transitions with respect to the $\Delta M = \pm 1$ transitions. As known in the art, the $\Delta M = 0$ absorptions reach a maximum when the optical radiation is polarized parallel to the field $\vec{F}$, whereas the $\Delta M = \pm 1$ absorption reaches a maximum when the optical radiation is polarized perpendicular to $\vec{F}$; hence, the opposite phases of response in FIG. 2 are obtained. The signal-to-noise ratio obtained in this way was 500:1 for the $M = 5/2 \leftarrow 3/2$ transition as compared with a ratio of 250:1 under similar conditions except using intensity modulated light rather than polarization modulated light.

Although the invention has been described in terms of a specific embodiment, various modifications can be made without departing from the scope of the invention. For example, instead of modulating the optical polarization, the modulator 12 can take the form of a rotating mechanical chopper, Pockel cell, or acousto-optic device for modulating the intensity of the optical beam 11.1. The dielectric layer 23 can be an electret material, thereby avoiding the need for the bias supply 25 and effectively providing higher voltage biases for greater microphone sensitivity. Instead of the microphone consisting of elements 22, 23, 24, small commercially available electret or other microphones could be used in conjunction with absorption cell 20. A static or modulated electric field $\vec{F}$ can be used instead of a magnetic field, allowing the Stark effect instead of the Zeeman effect of the impurity to be used in a similar way. The absorption cell can be placed within the laser cavity itself, thereby enabling increased intensity of optical radiation and hence enhanced sensitivity of response. Also, instead of detecting nitric oxide, this invention can be used to detect a variety of impurities such as CO, $CO_2$, H, OH, $HO_2$, $NO_2$, $N_2O$, Cl, and ClO in the air (including the stratosphere). Pure rotational transitions of these and other impurities in the microwave and far infrared regions, as well as atomic transitions in the near infrared and visible regions of the electromagnetic spectrum, could be used instead of the above-described infrared vibrational transitions. Although the magnetic field could be modulated at an acoustic frequency instead of modulating the optical beam, thereby bringing the absorption line periodically into and out of the coincidence with the laser wavelength, the microphone output would suffer from spurious background pickup directly from the oscillating magnetic field itself.

What is claimed is:

1. In combination:
   (a) an optical absorption cell containing a gas medium to be analyzed for an impurity;
   (b) means for forming a modulated beam of optical radiation containing a first optical wavelength, said beam modulated at a first acoustic frequency, in order to form a modulated optical beam incident on the absorption cell;
   (c) means for producing a static field in the gas medium having a field strength suitable for increasing the absorption by the impurity in the gas medium of energy at said first wavelength from the modulated beam; and
   (d) means, coupled to said gas medium, for detecting the pressure variations at said acoustic frequency of said gas medium in response to the said beam in the presence of said static field.

2. The combination recited in claim 1 in which the beam is modulated at said first acoustic frequency with respect to optical polarization of the said beam.

3. The combination recited in claim 1 in which the static field is a magnetic field.

4. The combination recited in claim 3 in which the beam is modulated with respect to its optical polarization, at said first acoustic frequency.

5. The combination recited in claim 1 in which the means for detecting includes a microphone.

6. In combination:
   (a) a source of a beam of electromagnetic radiation containing a first component at a first wavelength;
   (b) means located in the path of said beam for modulating said beam at an acoustic frequency to produce a modulated beam of electromagnetic radiation;

(c) an absorption cell, containing a gas medium to be analyzed for an impurity, located in the path of said modulated beam;

(d) means for producing a static electric field in the gas medium having a field strength suitable for enhancement of absorption by the impurity in the gas medium of electromagnetic energy from said first component in the modulated beam; and (e) means, coupled to said gas medium, for detecting the pressure response at said acoustic frequency of said gas medium in response to the said beam in the presence of said field.

7. The combination recited in claim 6 in which said source provides an optically polarized beam and in which said means for modulating said beam modulates the polarization of the said beam.

8. A method for detecting an impurity in a gaseous medium comprising the steps of:

(a) directing a beam of electromagnetic radiation, which is modulated at an acoustic frequency, upon the medium;

(b) applying a static field to the medium during step (a) of sufficient field strength to enhance the absorption by the impurity of said radiation; and (c) monitoring the pressure response of the medium at said acoustic frequency.

9. The method of claim 8 in which the beam is modulated with respect to its polarization.

10. The method of claim 8 in which the field is a magnetic field and the impurity exhibits a significant Zeeman effect.

11. The method of claim 8 in which the field is an electric field and the impurity exhibits a significant Stark effect.

* * * * *